US00PP19135P2

(12) United States Plant Patent
Kleinhanns

(10) Patent No.: US PP19,135 P2
(45) Date of Patent: Aug. 19, 2008

(54) ***PETUNIA* PLANT NAMED 'GLOW HOT PINK'**

(50) Latin Name: *Petunia hybrida*
Varietal Denomination: Glow Hot Pink

(75) Inventor: Christoph E. Kleinhanns, Gernrode (DE)

(73) Assignee: Hamer Bloemzaden B.V., H. I. Ambacht (NL)

( * ) Notice: Subject to any disclaimer, the term of this patent is extended or adjusted under 35 U.S.C. 154(b) by 0 days.

(21) Appl. No.: 11/827,189

(22) Filed: Jul. 11, 2007

(51) Int. Cl.
*A01H 5/00* (2006.01)

(52) U.S. Cl. ..... Plt./356

(58) Field of Classification Search ..... Plt./356
See application file for complete search history.

(56) References Cited

U.S. PATENT DOCUMENTS

PP16,468 P3 * 4/2006 Miyazaki et al. ..... Plt./356

* cited by examiner

*Primary Examiner*—Wendy C. Haas
(74) *Attorney, Agent, or Firm*—Jondle & Associates, P.C.

(57) ABSTRACT

A *petunia* cultivar particularly distinguished by very early flowering, large bright pink flowers and a compact plant habit is disclosed.

2 Drawing Sheets

Genus and species: *Petunia hybrida.*
Variety denomination: 'Glow Hot Pink'.

BACKGROUND OF THE NEW PLANT

The present invention comprises a new and distinct cultivar of *petunia,* botanically known as *Petunia hybrida,* and hereinafter referred to by the cultivar name 'Glow Hot Pink'. 'Glow Hot Pink' originated from a hybridization in May 2002 in Quedlinburg, Schsen-Anhalt, Germany. The female parent was a *petunia* with pink flowers while the male parent was a *petunia* with light lilac flowers.

The new cultivar was first propagated in summer of 2006 from mother stock and has been asexually reproduced through vegetative cuttings for five generations. The present invention has been found to retain its distinctive characteristics.

SUMMARY OF THE INVENTION

The following are the most outstanding and distinguishing characteristics of this new cultivar when grown under normal horticultural practices in Quedlinburg, Germany.

1. Large bright pink flowers;
2. Early flowering; and
3. Compact plant habit;

DESCRIPTION OF THE PHOTOGRAPHS

This new *petunia* plant is illustrated by the accompanying photographs which shows blooms and foliage of the plant in full color, the colors shown being as true as can be reasonably obtained by conventional photographic procedures.

DESCRIPTION OF THE NEW CULTIVAR

Figure 1:
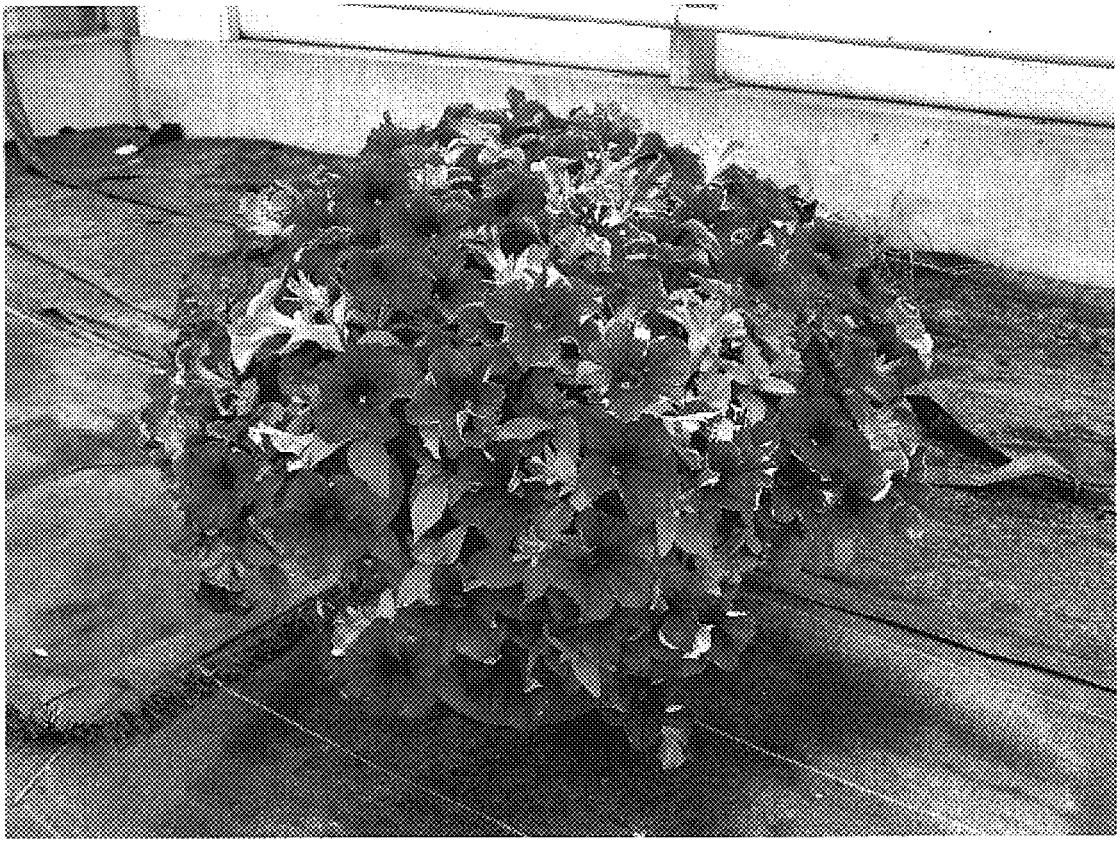
FIG. 1 shows the overall plant habit, including blooms, buds and foliage.
Figure 2:
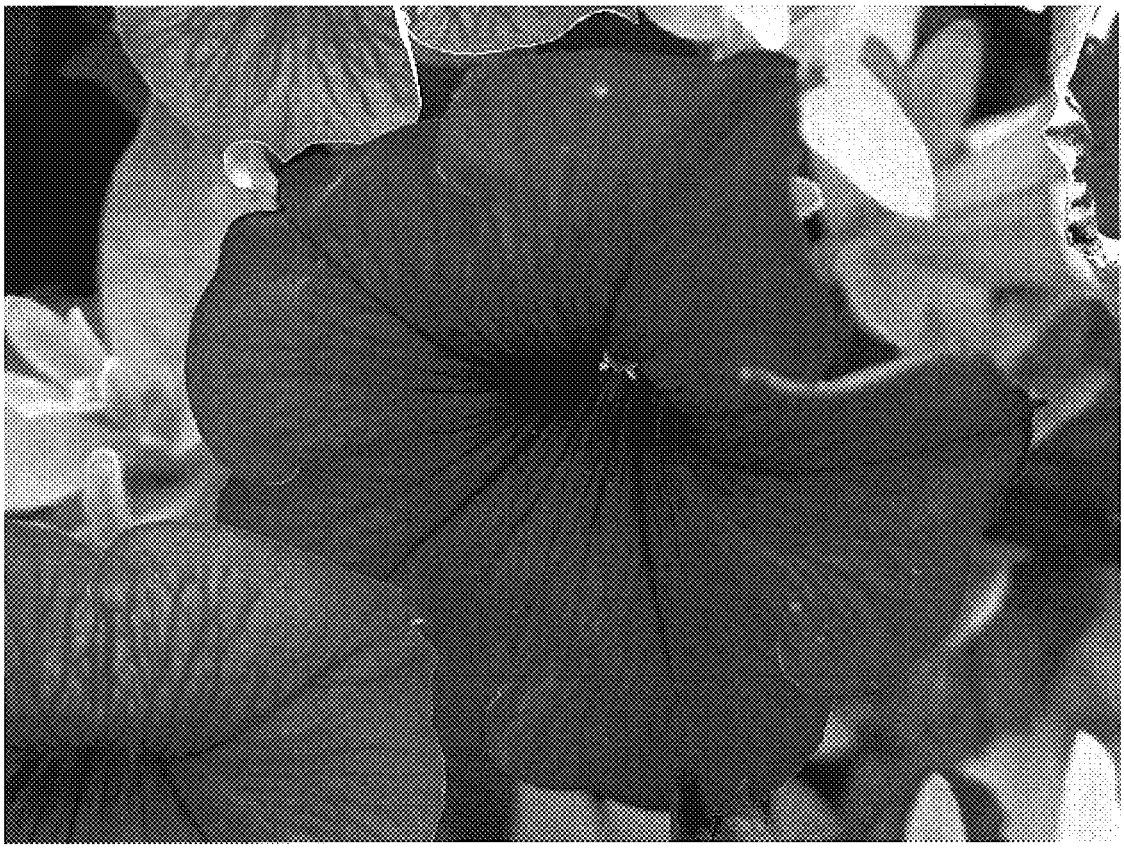
FIG. 2 shows the mature inflorescence.

The following detailed descriptions set forth the distinctive characteristics of 'Glow Hot Pink'. The data which define these characteristics were collected from asexual reproductions carried out in Quedlinburg, Sachsen-Anhalt, Germany. Data was collected on plants in 12 inch pots in October. Color references are primarily to the R.H.S. Colour Chart of The Royal Horticultural Society of London (R.H.S.) ($4^{th}$ ed). Anatomic labels are from *The Cambridge Illustrated Glossary of Botanical Terms,* by M. Hickey and C. King, Cambridge University Press.

DETAILED BOTANICAL DESCRIPTION

Classification:
- *Family.*—Solanaceae.
- *Botanical.*—*Petunia hybrida.*
- *Common name.*—*Petunia.*

Parentage:
- *Female parent.*—A pink-flowered *petunia.*
- *Male parent.*—A light lilac-flowered *petunia.*

Plant:
- *Form.*—Trailing.
- *Habit.*—Upright, later trailing.
- *Height.*—10.0 cm to 25.0 cm.
- *Width.*—Radius: 25.0 cm to 40.0 cm. Diameter: 50.0 cm to 80.0 cm.
- *Propagation.*—Terminal tip cuttings.
- *Time to produce a finished flowering plant.*—10 to 12 weeks.
- *Time to initiate and develop roots.*—4 to 5 weeks.
- *Root description.*—Fine rooting system, with white to light brown roots.

Stems:
- *Average number (basal).*—5 to 20.
- *Length of basal branches.*—40.0 cm to 70.0 cm.
- *Internode length.*—1.5 cm to 4.0 cm.

*Diameter of branches.*—Radius: 0.2 cm to 0.4 cm. Diameter: 0.4 cm to 0.8 cm.
*Stem color.*—RHS 141C (Green).
*Anthocyanin.*—Absent.
*Texture.*—Pubescent.

Leaves:
*Arrangement.*—Alternate.
*Size.*—Length: 3.0 cm to 6.0 cm. Width: 1.5 cm to 3.5 cm.
*Shape.*—Oval to longish, sometimes running spiky to the apex.
*Margin.*—Entire.
*Apex.*—Spiky.
*Base.*—Longish running to the stem.
*Immature leaf.*—General color: RHS 137A (Dark green). Upper surface: RHS 141C (Light green). Lower surface: RHS 139B (Green).
*Mature leaf.*—General color: RHS 137A (Dark green). Upper surface: RHS 141C (Light green). Lower surface: RHS 139B (Green).
*Texture.*—Pubescent, soft, mucilaginous.
*Venation.*—Indistinct.
*Venation color.*—Upper surface: RHS 139C (Light green). Lower surface: RHS 139D (Light green).
*Petioles.*—Leaves nearly direct on the branches.

Flower bud:
*Shape.*—Long tube.
*Size.*—Length: 4.0 cm to 6.0 cm. Radius: 0.1 cm to 0.3 cm. Diameter: 0.3 cm to 0.6 cm.
*Color of tight buds.*—RHS 59A (Dark red-violet) with RHS 139B (Green).
*Immature flower color.*—RHS 59A (Dark red-violet).

Inflorescence:
*Blooming habit* (*flowering season*).—May to November.
*Inflorescence type.*—Single flowers.
*Number of flowers per node.*—1.
*Lastingness of individual blooms on the plant.*—about 7 days, but very much dependent on irrigation, fertilizer and temperature.
*Fragrance.*—Soft.
*Pedicels.*—Color: RHS 139B (Green). Length: 0.5 cm to 2.0 cm. Diameter: Radius: 0.1 cm to 0.15 cm. Diameter: 0.2 cm to 0.3 cm. Texture: Pubescent.

Flowers:
*Shape.*—Funnel shaped.
*Size.*—Diameter (flower face): Radius: 3.5 cm to 5.0 cm. Diameter: 7.0 cm to 10.0 cm. Depth (total length of flower): 5.0 cm to 7.0 cm. Funnel: Length: 3.0 cm to 4.0 cm. Diameter (at opening): Radius: 0.4 cm to 0.7 cm. Diameter: 0.8 cm to 1.4 cm. Outside texture: Pubescent. Outside color: RHS N66D (Soft pink).
*Mature flower.*—Face/Margin Color: RHS 66B (Pink). Upper surface: RHS 66A (Pink). Lower surface: RHS 145B (Light yellow-green). Corolla tube: Shape of corolla: Open, funnel shaped. Color inside (throat): RHS 85A (Violet veined). Color outside: RHS 64C (Pink). Petals: Apex: Round. Base: Fused. Margin: Entire. Waviness; Moderate. Lobation: Moderately lobed. Texture: Smooth.
*Calyx arrangement.*—Symmetric.
*Sepals.*—Number: 5. Color: RHS 149D (Light yellow-green). Length: 2.0 cm to 3.0 cm. Width: 0.3 cm to 0.7 cm. Shape: Not fused, longish. Apex: Spiky. Base: Longish. Margin: Entire. Texture: Pubescent.

Reproductive organs:
*Stamens.*—Quantity: 5. Shape: Cylindrical. Color: RHS 142B (Green). Filament length: 0.8 cm to 1.5 cm. Filament diameter: Radius: Less than 0.1 cm. Diameter: Less than 0.1 cm.
*Anther.*—Shape: Oval. Color: RHS 155A (Cream). Length: 0.2 cm to 0.4 cm. Diameter: Radius: 0.1 cm to 0.15 cm. Diameter: 0.2 cm to 0.3 cm.
*Pollen.*—Color: RHS 155A (Cream). Amount: Abundant.
*Pistils.*—Number: 1. Length: 1.5 cm to 2.5 cm. Diameter in cm: Radius: Less than 0.1 cm. Diameter: Less than 0.1 cm. Stigma: Color: RHS 142B (Green). Shape: Oval. Length: 0.1 cm to 0.2 cm. Diameter: Radius: 0.1 cm to 0.15 cm. Diameter: 0.2 cm to 0.3 cm. Style: Color: RHS 149D (Light yellow-green). Length: 1.4 cm to 2.3 cm. Diameter: Radius: Less than 0.1 cm. Diameter: Less than 0.1 cm. Shape: Long cylindrical.

Seeds:
*Color.*—RHS 175A (Dark orange-brown).
*Length.*—Less than 0.1 cm.
*Diameter.*—Radius: 0.1 cm. Diameter: 0.1 cm.
*Shape.*—Round.

Disease and insect resistance: Resistance and susceptibility is typical of the species.

COMPARISON WITH KNOWN CULTIVARS

'Glow Hot Pink' differs from the female parent *petunia* plant in that the female parent has a more upright growth habit than 'Glow Hot Pink'.

'Glow Hot Pink' differs from the male parent *petunia* plant in that the male parent has a light lilac flower color, while 'Glow Hot Pink' has a pink flower color.

'Glow Hot Pink' differs from commercial *petunia* variety 'SURFINIA Crazy Pink' U.S. Plant Pat. No. 16,468 in that 'Glow Hot Pink' has a flower color of RHS 66A, while 'SURFINIA Crazy Pink' has a flower color of RHS 67B.

I claim:

1. A new and distinct cultivar of *petunia* plant as described and shown herein.

* * * * *